United States Patent [19]

Draenert

[11] Patent Number: 5,084,050
[45] Date of Patent: Jan. 28, 1992

[54] IMPLANT FOR BONE REINFORCEMENT AND FOR ANCHORING BONE SCREWS, IMPLANTS AND IMPLANT PARTS

[76] Inventor: Klaus Draenert, Gabriel-Max-Str. 3, 8 München 90, Fed. Rep. of Germany

[21] Appl. No.: 418,705

[22] Filed: Oct. 2, 1989

Related U.S. Application Data

[63] Continuation of Ser. No. 256,252, Oct. 6, 1988, abandoned, which is a continuation of Ser. No. 902,447, filed as PCT/EP85/00710, Dec. 16, 1985, abandoned.

[30] Foreign Application Priority Data

Dec. 14, 1984 [DE] Fed. Rep. of Germany ....... 3445738

[51] Int. Cl.$^5$ ............................................. A61B 17/58
[52] U.S. Cl. ........................................ 606/77; 606/73; 606/63
[58] Field of Search ............... 606/76, 77, 60-66; 623/22, 23

[56] References Cited

U.S. PATENT DOCUMENTS

| | | | |
|---|---|---|---|
| 2,381,050 | 8/1945 | Hardinge | 128/92 R |
| 4,259,072 | 3/1981 | Hirabayashi et al. | 606/65 X |
| 4,351,069 | 9/1982 | Ballintyn et al. | 128/924 F |
| 4,483,678 | 11/1984 | Nishio et al. | 128/924 F |
| 4,542,539 | 9/1985 | Rowe, Jr. et al. | 606/76 X |
| 4,550,448 | 11/1985 | Kenna | 606/76 X |
| 4,599,085 | 7/1986 | Riess et al. | 128/924 F |
| 4,612,923 | 9/1986 | Kronenthal | 128/927 R |
| 4,640,271 | 2/1987 | Lower | 128/924 F |
| 4,655,777 | 4/1987 | Dunn et al. | 606/77 X |

FOREIGN PATENT DOCUMENTS

| | | |
|---|---|---|
| 0077868 | 10/1981 | European Pat. Off. |
| 2084468 | 9/1981 | United Kingdom |

OTHER PUBLICATIONS

"The Condensed Chemical Dictionary" 10th edition by Gessner G. Hawley, 1981, p. 492.
"2267 Engineering in Medicine" vol. II (1982) No. 4 *A Proposed Design for an Expanding Hip Nail* by D. Raftopoulous, J. D. Baril. pp. 187-188.

*Primary Examiner*—Mickey Yu
*Assistant Examiner*—Kevin C. Kooney
*Attorney, Agent, or Firm*—Kinney & Lange

[57] ABSTRACT

The invention relates to an implant (10) to sheath and-/or reinforce bone and/or to anchor bone screws. The implant (10) takes the shape of a dowel which is capable of spreading and/or swelling and/or interlocking in bone in some other way. The implant (10) preferably presents ring-like bulges (16) on its outer surface and an internal screw thread (20) on its inner surface to screw in bone screws. Implant (10) improves the tensile strength when anchoring bone screws (Figure 1).

35 Claims, 3 Drawing Sheets

IMPLANT FOR BONE REINFORCEMENT AND FOR ANCHORING BONE SCREWS, IMPLANTS AND IMPLANT PARTS

This is a continuation of application Ser. No. 07/256,252 filed on Oct. 6, 1988, abandoned as of the date of this application, which is a continuation of application Ser. No. 06/902,447 filed as PCT/EP85/00710, Dec. 16, 1985, now abandoned.

BACKGROUND OF THE INVENTION

1. Field of the Invention

The invention relates to an implant to sheath and/or reinforce bone and/or to anchor bone screws.

2. Description of the Prior Art

Various healing forms can be identified in bone fractures and bone gaps. In accordance with the histological picture, a distinction is made between spontaneous bone healing and direct bone formation. The major differences are that in spontaneous bone healing cartilage and fibrous connective tissue are formed; the latter is converted to woven bone and lamellar bone tissue by means of re-differentiation In direct bone formation woven bones are formed directly in the case of large gaps and lamellar bones in the case of small gaps as a result of the high mechanical stability. The advantages of direct bone healing are due to the shortened healing time, i.e. bone bridging is achieved at an early stage. This guarantees very early mobilization and stability during exercise.

When fractures are treated conservatively, it is primarily spontaneous bone healing which occurs. This is why complications often result. These may include delayed or non-existent bone healing or non-union.

Generally speaking, direct bone healing cannot be achieved without operative repair and stable fixation by means of screws and plates. The interfragmentary compression required to guarantee mechanical stability is achieved by pre-loading the plate with a plate tension device or by means of the dynamic compression plate and an interfragmentary screw, in particular a screw with a tension or gliding hole, or also by means of "fixateurs externes".

These operation techniques were developed primarily by the Association for the Study of Internal Fixation. The histological picture of this type of bone healing is direct bone healing with no or very little callus formation. Bone grows through the remodelling units of the Haversian canals at the level of the fracture line. Bone screws with pre-cut threads have a firm support in the compact cortical bone. Cancellous bone screws with a widely projecting thread and a nearly rectangular pressure rest are used in the metaphyseal bone sections filled with cancellous bone. These screws are meant to interlock in the trabeculae.

Tensile tests and torque measurements have shown, however, that the cancellous bone in the metaphyses and the areas near the joints does not present the screws with any resistance whatsoever. As a result, the screws cannot build up any tension in the elastic cancellous bone. The tensile stress produced by the screws is eliminated within a few seconds. The screws cannot serve to fix the fragments mechanically, since they do not exert any interfragmentary compression. This is of particular practical importance when poorly positioned fragment ends are to be fixed one on top of the other by means of interfragmentary tension emanating from the screws.

This is often necessary in certain types of fractures of the femoral neck, for instance. A necrosis of the entire epiphyseal section, i.e. necrosis of the head of the femoral neck, frequently results from insufficient fixation in this region. This often makes prosthetic replacements necessary, even in young patients. Only in very young individuals do cancellous bones screws have any support in the cancellous bone of the metaphyses, thus making it possible to demonstrate tensile stress for a number of minutes.

In older and elderly individuals, the trabeculae are very often scarce, so that even normal screws cannot be supported in the compact substance. In such cases, many attempts have been made to reinforce the osteosynthesis with plates and screws by means of an association with bone cement. The medullary cavity was filled with bone cement and the bone screws were fixed in the hardened cement. The drawback involved in this method, in particular for younger patients, is the fact that the bone cement cannot be removed. It remains in the medullary cavity section as a foreign body for the rest of the patient's life.

Similar problems are encountered when treating epiphyseal closures. The epiphyseal cartilage can also be locked contralaterally in unilateral epiphyseal fractures which often lead to unequal growth. Screw fixation sometimes suffices for this purpose, but frequently only partial closure is achieved as a result of unequal tension from the screws. This in turn leads to scoliosis. Similar problems occur when arthrodeses, i.e. artificial ankyloses, are performed. These are performed in cases in which joint movability is no longer desired since it disturbs joint stability. This type of arthrodesis has only been achieved in rare cases with screws, since in the course of time the screws loosened. Similar problems are involved in preventing the risk of microfractures in supporting epiphyseal structures or the risk of necroses in the head of the femoral neck. This is generally followed by the complete destruction of the hip joint. For example, depressed bone parts are supported or lifted, or torn bony tendon or ligament insertions are re-inserted post-traumatically.

Thus, the problem to be solved by the invention is to prepare surgical material which guarantees the secure fixation of bone screws and plates, in particular in bone sections near the joints. With this material, endangered or depressed bone parts are to be supported.

The problem is solved in particular by the features of the patent claims.

SUMMARY OF THE INVENTION

The invention is based on the fundamental idea of preparing an implant to sheath, support and/or reinforce a bone after being inserted therein; said implant must have a firm support in the surrounding bone and in turn also provide a screw with long-term support and tensile strength. The firm support in the bone is guaranteed in particular by the fact that the implant either spreads out when a screw is screwed in, or expands, or swells as a result of its material properties when it comes into contact with the body fluids in the bone, or it is screwed in itself. In this way, the surgical material inserted in the form of an implant is interlocked, blocked or generally firmly lodged. The outer surface of the implant is preferably structured, for example by grooves and/or perforations. The implant's anchoring in the bone improves with increased structuring and the tensile strength as well as the force required to remove a screw anchored in the implant is increased.

The implant preferably takes the shape of a hollow body. The hollow body can be securely anchored in the bone by screwing in a bone screw or locking a wedge, peg or bone cylinder such as a cartilage bone cylinder or a ligament bone cylinder, or by inserting, screwing in or injecting an interchangeable medication and/or radiation therapy vehicle. The hollow body s lumen is provided with the appropriate internal structure for this purpose. The internal structure can, for example, be an internal screw thread or a thread-like structure for a bone screw, or a coarse, irregular structure with elevations and impressions by means of which an inserted wedge or cylinder can be held in place and which expands the hollow body upon insertion. A particularly preferred embodiment of the implant takes the form of a structured, unilaterally closed hollow cylinder. This type of implant will also be referred to as a bone dowel in the following. The dowel-like implants of the invention are used wherever osteotomies or fractures affect the epiphyseal or metaphyseal region. The bone dowel is placed through a drilled hole in the contralateral fragment. The bone screw equipped with a collar is then screwed in. The bone dowel is then securely and firmly fitted in its half of the fracture and thus contributes to building up the required interfragmentary compression. The inner diameter of the dowel is preferably somewhat smaller than the outer diameter of the cancellous bone screw to be screwed in. The difference could amount to approximately 2 mm, for instance. In this way, the dowel spreads out when the screw is screwed in and is firmly locked in the cancellous bone. A cancellous bone screw fixed in this way exhibits considerably increased long-term tensile strength. This can be demonstrated on the basis of drawing tests. The individual fragments can be fixed mechanically with the bone dowel of the invention even in poorly positioned fracture lines. This prevents the necrosis of the epiphyseal section in fractures of the femoral neck, for example. With the dowel implant of the invention, even normal cancellous bone screws find sufficient support in the scarce cancellous bone at the head of the femoral neck in older patients. The rate of poor results can be reduced substantially due to the stability of the screw. When the dowel implants of the invention are used, two or three screws generally suffice, even in complicated types of fractures, to obtain stable screw fixation.

When treating epiphyseal closures and unilateral ephiphyseal fractures, the use of the bone dowel of the invention creates such high pressure in the epiphyseal cartilage that uniform bone formation in the epiphyseal growth plate results. The dowel implant of the invention also permits the stable locking of screws in scarce, osteoporotic bone in older and elderly patients. Thus, even in such cases, it is not necessary to use a framework osteosynthesis with bone cement to fix the bone screws.

Using the dowel implant of the invention, arthrodeses can also be performed by means of screws. Such high pressures are produced in the joint space when the screws are anchored in the implant that bone formation sets in immediately and bone structures begin to grow through the joint.

An additional indication for the dowel implants of the invention is to support segments running the risk of developing microfractures. An example for this is the spherical sector of the head of the femoral neck when the head has undergone necrosis. In this case, it is preferable to screw a bone screw of the same material as the implant into the dowel which thus supports the spherical sector. In this way, one or two dowel implants can fully heal the imminent necrosis of the head. The screw and dowel combination supports the bearing epiphyseal structures like a pillar.

There is a particular application for dowel implants provided with an antibiotic such as gentamycin. These implants serve not only to stably fix and anchor bone screws; they also serve as drug applicators to control osteitis. The dowel implants of the invention serve as direct anchors in the cancellous bone in cases of torn ligaments, reinserted tendons, apophyses and epicondyles. Specific indications include: fixing sockets and trochanters in total prostheses, fixing trochanters during repeated operations and the general anchoring of components in artificial joints which are screwed in or interlocked.

A specific dowel shape is a hollow cylinder structured on the inside and outside which is capable of stably fixing bone cylinders, cartilage bone cylinders and ligament bone cylinders in the implant. If these dowels are perforated and if they consist of an absorbable material, they will lead to a rapid bony ingrowth into the transplant or the re-inserted bone cylinder. Fracture lines can be bridged over by bone formation when such bone cylinders are used in conjunction with the dowels. The dowel implants of the invention can be made of various materials such as metal or plastic, preferably of a biocompatible plastic of sufficient mechanical strength and resistance. Plastic dowels with precise dimensions can be made in a simple mechanical way by means of milling. They can also be made by injection moulding when the appropriate plastics are used. Preferred plastics include: high density polyethylenes, polyacetates, Teflon products, polyester, polymethane, carbon or frameworks of these plastics with ceramics, bioglasses and apatites.

The preferred forms and shapes of such plastic dowels, in particular their inner and outer contours and profiles, will be described in more detail in the following. Metal and plastic implants present one disadvantage, however: They either remain in the body as a foreign body or they are removed with the screw, which leads to at least a partial destruction of the cancellous bone structure formed after the fracture has healed. For this reason, non-absorbable plastic or metal dowels are used primarily in older or elderly patients in the treatment of fractures of the femoral neck, for example. When bone screws are used in the cancellous area in younger patients, it is best to use absorbable materials. Preparing such absorbable materials for dowel implants is also an object of the present invention.

The absorbable surgical material of the invention used to prepare the dowel implant of the invention is preferably based on polylactates, polyglycolates, polypeptides, collagens, apatites or absorbable ceramics or frameworks of two or more materials. Some of the above-mentioned materials can be easily liquified and processed using casting or injection moulding methods. Any desired shape can be produced. In this way, very stable, rigid and resistant bone implants can be prepared. They can be structured just as easily as plastic dowels produced using mechanical methods.

A stabilizing and bioactivating filler is preferably added to the base material forming the absorbable matrix of the implant. Said filler is preferably a sintered or flushed hydroxyl apatite or absorbable tricalcium phosphate. A 5–50% by weight share is preferably added. This leads to an accelerated incorporation of the implant and to reinforced osteogenesis. The filler can be added to the molten mass of the base material and cast or injected in an injection mould under pressure. The filler preferably takes the form of spheres 10–200 pm, preferably 5–30 pm, in size. The filler should present a high pore volume, preferably accounting for approximately 25–65% and more preferably over 40% of the total volume.

The above-mentioned absorbable materials present the following advantage: They are capable of swelling when they come into contact with the body fluids; collagens are more capable of swelling than polyglycolates. Due to its swelling capability, the dowel implant has an excellent mechanical anchoring in the bone. In addition, the tissue is subjected to tranverse extension as a result of the implant's swelling. This leads to an additional, even stronger bone-forming effect. The stimulus resulting from the extension of the implant leads to considerably accelerated osteogenesis, as has been confirmed in animal experiments. Direct bone appositions are deposited on the implant surface after only a few days. The implant is stably integrated with bone along its entire surface. A bone screw screwed into this type of dowel implant presents significantly higher tensile strength in drawing tests when compared to bone screws which have not been secured with dowels. The above-mentioned absorbable materials are absorbed for the most part within approximately 90 days.

The implant material can be reinforced by a sheath in the form of fibers, fiber networks or tissues to achieve particularly stable implants. Said sheaths can also be made of an absorbable or non-absorbable material.

A pharmaceutical substance such as an antibiotic and/or a cytostatic agent and/or a bone morphogenetic protein and/or a hemostatic agent and/or a hormone, a chemotherapeutic agent or a biologically active substance can be added to the implant material of the invention in a particularly advantageous way. Polyglycolate is a particularly suited base material for this purpose since its melting temperature does not exceed the temperature which would destroy conventional antibiotics such as gentamycin. Implant dowels with this type of admixture not only result in a stable mechanical fixation. In cases of infected non-union, for example, they also serve as an effective local therapy of the infection.

The implant of the invention can present various outer forms. What is important is that the implant interlocks rigidly and mechanically with the surrounding bone as a result of spreading, expanding or swelling. This then serves to support the bone and/or anchor a bone screw. The outer surface of the implant is preferably structured, for example with grooves, projections and/or perforations to improve the mechanical interlocking. The structuring can either be along the axis of the implant, i.e. in the direction in which the implant is inserted in the bone, or perpendicular thereto along the implant's circumference, or at any desired angle.

Structuring on the implant surface has an additional advantage: Bone ingrowth is induced. Generally speaking, implant structures can be broken down into 1st to 4th order structures. On the basis of this definition, the 1st order structure is the outer implant design, the 2nd order structure the topography of the implant, in particular surface shapes such as wave or saw tooth-like shapes in the implant sections, the 3rd order structure the surface microstructure in the millimeter or submillimeter range and the 4th order structure is the ultrastructure of the surface with structural elements in the magnitude of approximately 10–200 pm, preferably 20–30 $\mu$m. The 3rd and 4th order structures are particularly important for optimal bone formation and bone ingrowth. The implants of the invention preferably present 3rd and 4th order surface structures. When the implant of the invention takes the form of a unilaterally closed, structured hollow cylinder, the 3rd order structure is preferably represented by several tire-like rings or bulges around the cylinder's circumference. Preferably, there are several of these bulges arranged regularly and one on top of another along the cylinder's axis, thus giving it the appearance of stacked tires.

The diameter of a tire cross-section or the tire distance is approximately 200–3,000 pm, preferably approximately 500–2,000 pm. The outer surface of the rings facing the bone is nearly semi-circular.

As an alternative or in addition to this shape, the structuring can also take the shape of spheres or spherical sections, such as semi-spheres with a diameter of approximately 200–2,000 pm. There is accelerated bone ingrowth particularly when larger and smaller spheres are combined. A diameter ratio of 2:1 to 3:1 is especially good. For example, spheres with a diameter of from 200–1,000 pm mean: 500 pm can be combined with spheres with a diameter of from 800–3,000 pm mean: 1,000 pm). The smaller spheres preferably present a diameter of from 300–700 pm, more preferably from 450–550 pm and the larger spheres from 800–2,000 $\mu$m, more preferably from 900–1,200 $\mu$m. The smaller and larger spheres each preferably present approximately the same diameter, i.e. 500 $\mu$m and 1,000 $\mu$m. There is more rapid bone accumulation around the smaller spherical elements, whereas the supporting bone arches are formed around the larger spherical elements.

The surface of the spheres, spherical sections or bulges can be microstructured and the microstructure can take the shape of spheres or spherical sections such as semi-spheres with a diameter of between 10 and 50 pm, preferably between 15 and 30 $\mu$m. The spaces between the larger spheres or bulges and/or the surface of the implant can be filled and can be covered with a coating mass. This mass together with the approximate microstructure of the larger spheres or bulges represents the 4th order structure of the implant of the invention. The coating mass preferably consists of an organic, generally absorbable matrix and inorganic filler components or fillers.

The outer surface of the implant can either have a thick coating with a thickness of between approximately 300 and 2,000 pm or a thin coating with a thickness of between approximately 20 and 300 pm. The layer can either be closed and fully enclose the implant or may only cover parts of the implant. It can be applied directly or indirectly in a framework.

The fillers preferably consist of spherical particles with a diameter of between 10 and 200 $\mu$m, preferably between 15 and 50 $\mu$m and more preferably between 15 and 30 $\mu$m. To facilitate bone ingrowth, the larger particles in particular are preferably porous and present a pore volume of between approximately 25 and 65%. Said spheres are recognized as a base by osteoblasts and stimulate bone ingrowth. The fillers preferably consist of tricalcium phosphate, hydroxyl apatite or bioglass.

The matrix of the coating, which can also fill the pores of the highly porous fillers, preferably consists of a polypeptide, polylactate, polyglycolate or one of their co-condensates, gelatine, collagen and/or calcium compounds.

At least a part of the fillers can take the form of fibers with a thickness of between 100 and 300 μm, preferably approximately 200 μm and a length of greater than 2 and up to 15 mm, the preferred length being at least 3 mm and at most 10 mm, with the optimum length being approximately 4-5 mm. The fibrous fillers improve stability and preferably consist of the same materials as the spherical fillers. The fibers, particularly after they have been knit to form a framework, can serve as an outer sheath for the implant.

A pharmaceutical substance such as an antibiotic can also be added to the coating.

Particularly preferred is a microstructure which takes the form of spheres in a framework with an organic matrix layer.

BRIEF DESCRIPTION OF THE DRAWINGS

The invention will be explained in more detail in the following on the basis of the figures in which.

DETAILED DESCRIPTION OF THE PREFERRED EMBODIMENTS

Figure 1:
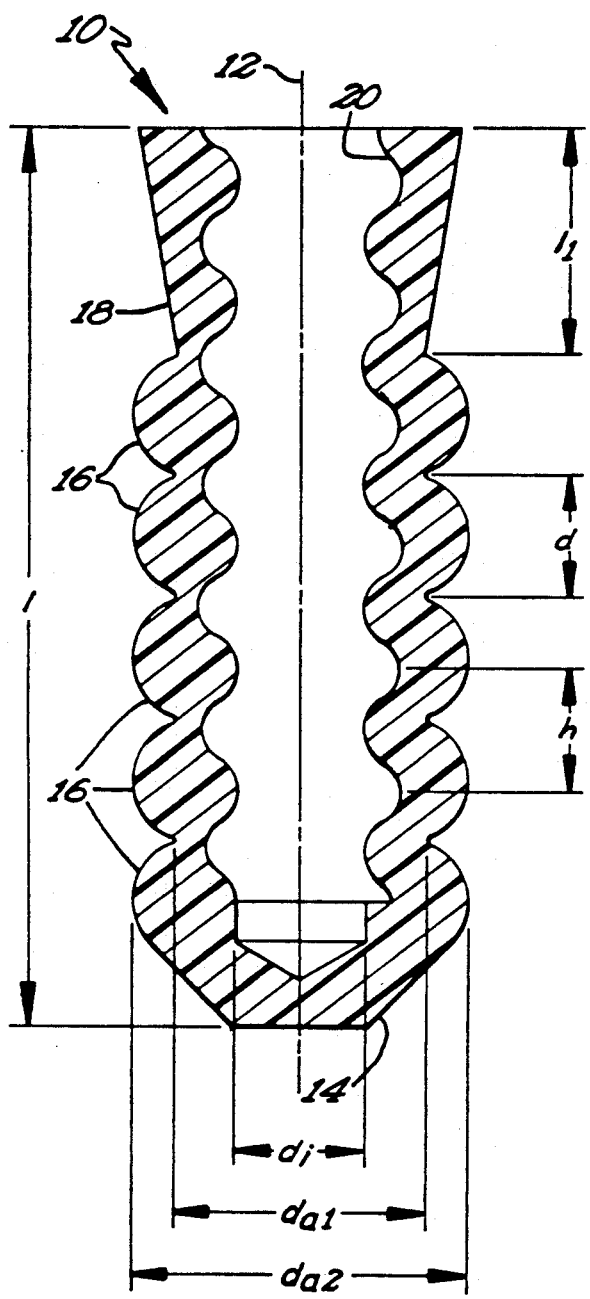
FIG. 1 is a longitudinal section of one embodiment of the implant according to the invention—a schematic drawing of a bone dowel.

Implant 10 in accordance with FIG. 1 takes the form of a structured hollow cylinder with axis 12. The bone dowel is cone-shaped at its tip 14 to facilitate its insertion into the bone. The cone is preferably at an angle of approximately 45° to axis 12.

The bone dowel presents several, preferably five or more rings or bulges 16 along its circumference. These are layered directly on top of one another in the axial direction. Thus, the circumference of the dowel s longitudinal section presents a profile consisting of adjacent semi-circles. The rear end section 18 of implant 10 also takes the shape of a cone. The cone-shaped end section 18 forms a smaller angle with axis 12 than does tip 14, the former angle being, for example, 10°-20°. The inside of implant 10 presents an internal screw thread 20 or a thread-like structure to screw in bone screws, e.g. cancellous bone screws.

Dowel implant 10 in accordance with FIG. 1 preferably presents the following approximate dimensions which have been adopted on the basis of conventional cancellous bone screw dimensions:

Length l: 16-32 mm
External diameter $d_{a2}$: 6-7 mm
Diameter $d_{a1}$: 4-5 mm
Internal diameter $d_i$: 2.5-3.5 mm
Bulge interval d: 0.5-3.0 mm
Lead h: 2.5-3 mm
Length $l_1$ of the end section: 4-6 mm
Wall thickness: 0.5-2.5 mm The diameter of the rings is somewhat greater than the bulge interval d (see dots in FIG. 1).

The implant's dimensions depend, of course, on the type of screw to be anchored or the type of bone to be supported. When screws are being anchored, the internal diameter of implant 10 is preferably somewhat smaller than the diameter of the bone screws. This causes implant 10 to spread out when the screw is screwed in. The external diameter $d_{a2}$ is approximately 4-4.5 mm when the implant is inserted in the compressed state.

Figure 2:
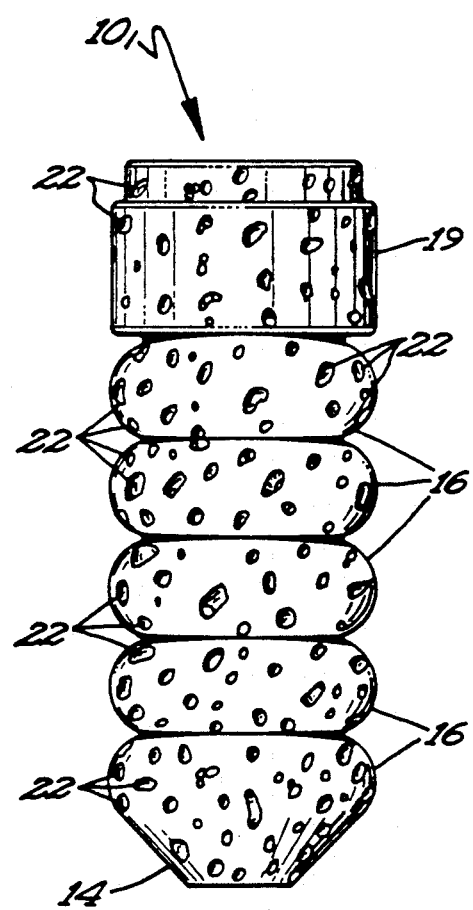
FIG. 2 is a side view of a bone dowel according to the invention.

Implant 10' in accordance with FIG. 2 corresponds for the most part with implant 10 in accordance with FIG. 1. The end section 19 of implant 10' is cylindrical. Moreover, perforations 22 are visible on the outer surface of implant 10'. Implant 10' may present small cylindrical spaces between the various bulges 16. Implants 10 and 10' in accordance with FIGS. 1 and 2 are made of tricalcium phosphate-polyglycolate with the share of tricalcium phosphate amounting to approximately 25%. The surface porosity can be adjusted according to the cooling rate of the gas-forming additives or gels. It can also be pre-set up to the 3rd order structure by the mould when gas-forming or easily vaporable substances are added.

Figure 3:
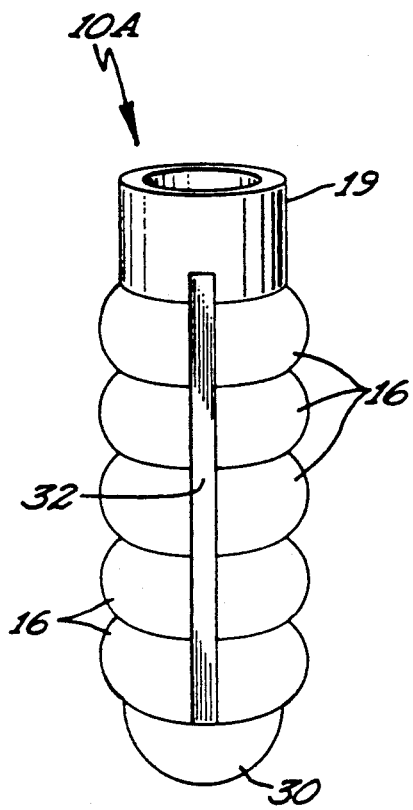
FIGS. 3—9 show further implants according to the invention.

Implant 10A in accordance with FIG. 3 also takes the form of a structured hollow cylinder with five bulges 16, a cylindrical end section 19 and a semi-spherical front end 30. A continuous axial groove 32 along the implant's longitudinal direction facilitates the compression of the implant when it is inserted into the bone.

Figure 4:
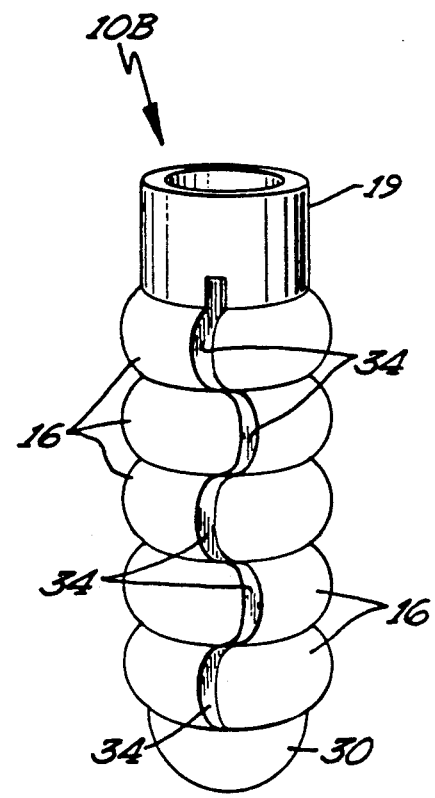

Implant 10B in accordance with FIG. 4 is also a hollow cylinder. It is different from implant 10A in that the axial grooves 34 in the individual bulges 16 are displaced along the circumference.

Figure 5:
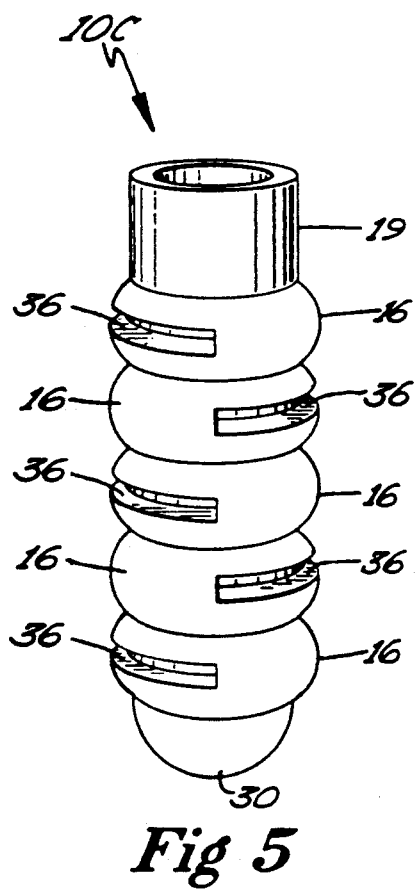

Every bulge 16 in implant 10C in accordance with FIG. 5 presents a transverse groove 36 along the implant's circumference.

To further facilitate the insertion of the implant into the bone and its spreading or swelling in the bone, the axial and transverse grooves presented in FIGS. 3-5 can be combined in a suitable way.

Figure 6:
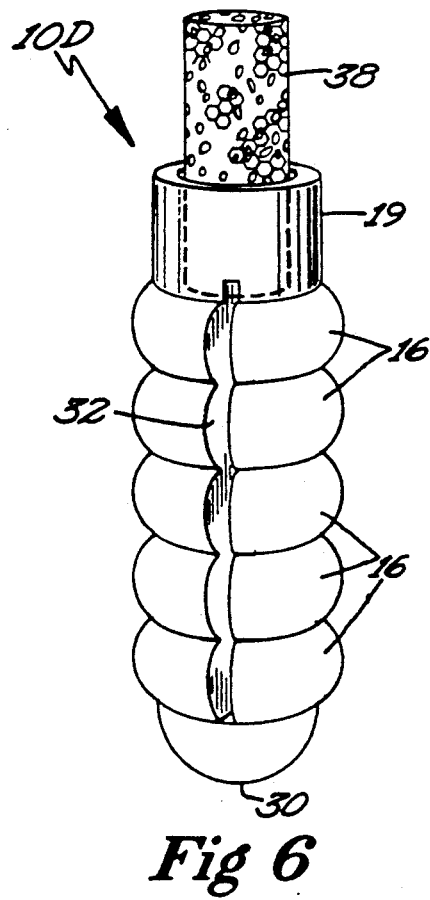
Figure 7:
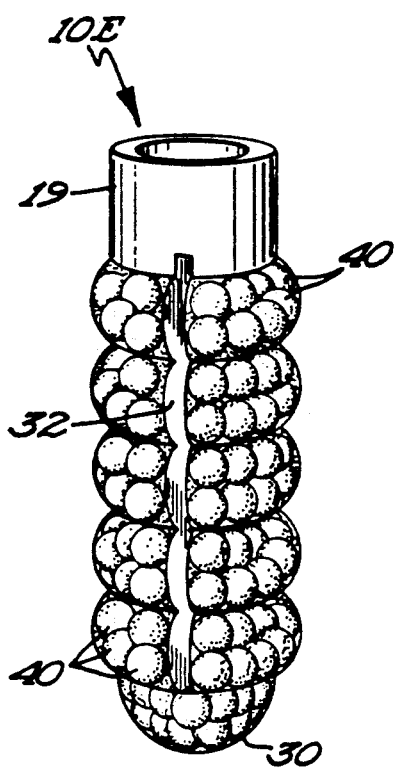

Implant 10D in accordance with FIG. 6 is also a hollow and cylindrical dowel. The implant supports an autologous bone cylinder 38 in its inner hollow space. Said cylinder can be stably fixed in the bone by means of the dowel. Implant 10D is preferably absorbable, thus permitting the re-inserted bone cylinder to undergo rapid bony ingrowth. Implant 10D can also support a medication and/or radiation therapy vehicle instead of bone cylinder 38. Implant 10E in accordance with FIG. 7 also presents a longitudinal groove 32. Said implant consists of a matrix made up of a framework of abutting spheres 40. The framework of spheres is held in place by the coating mass.

Figure 8:
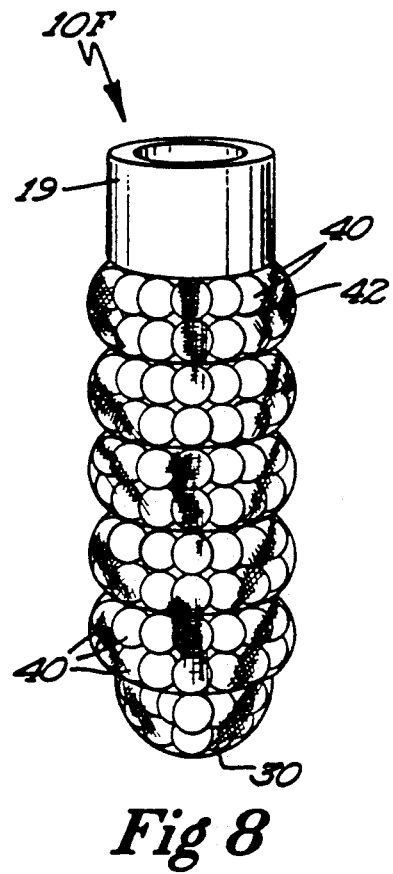

The pack of spheres consisting of a framework of spheres 40 is sheathed by network 42 in implant 10F in accordance with FIG. 8. Network 42 can also consist of knitted bead chains or extruded fibers or threads formed into a network. Said fibers or threads may also contain small spheres.

Figure 9:
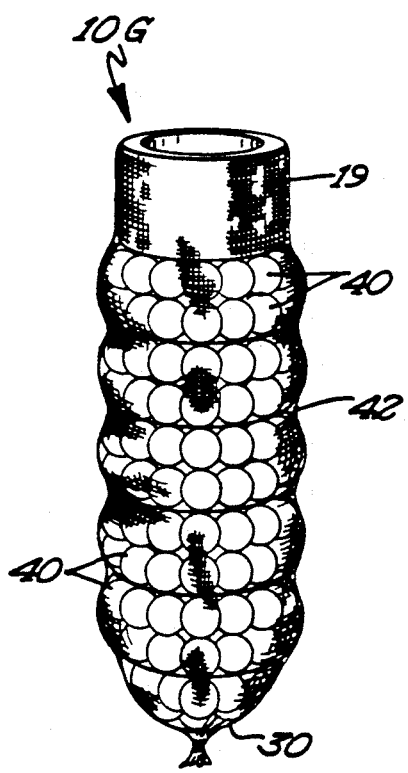

Loose spheres 40 are held in place in a double-walled stocking cage 42 consisting of knitted fibers or threads in implant 10G in accordance with FIG. 9. The spheres can be brought into close, mutual contact by turning stocking cage 42. The implant swells after being inserted in the bone and can be spread out and become interlocked in the bone by screwing in a screw or inserting a cylinder or wedge in its hollow inner space.

Tests were conducted on pigs' epiphyses in which osteotomies had been performed. Bone screws anchored with plastic dowels presented a tensile strength which had increased by more than 50%. It should be noted that the cancellous bone in pigs' epiphyses presents a very compact and solid bone structure. Since the tensile strength of cancellous bone screws anchored in human bones, in particular older bones, is virtually zero without the help of dowels, the use of the dowel implants of the invention to anchor cancellous bone screws in human bones can increase the tensile strength considerably, perhaps many times over. In the animal experiments, the tensile strength of the cancellous bone screws is measured as a function of time by connecting dynamometers to the screws.

The results with respect to tensile strength are similar for absorbable and plastic dowels.

The examples shall serve to explain the invention with the help of the production of embodiments of the implants according to the invention.

Producing a bone dowel:

EXAMPLE 1

2 g of polyglycolate granulate are mixed with several grams of biocompatible softeners in a crucible. These are melted at approximately 130° C. 0.5 g of finely pulverized tricalcium phosphate is added to the hot molten mass which is stirred until a homogeneous mass results. The hot molten mass is then poured into a metal form which was milled from aluminium or brass using precision mechanics. A dowel with a hollow cylinder and internal screw thread can be produced in the following simple manner: A commercial bone screw whose thread was milled down by approximately 1-2 mm is fit into the metal casting mould containing the hot molten mass. After the molten mass has cooled, the dowel and inserted screw are removed from the metal casting mould. The bone screw is then screwed out of the cooled molten mass.

EXAMPLE 2

The desired bulge-shaped or semi-spherically shaped surface structures are mechanically milled out of a block of high density polyethylene. The shape of the hollow cylinder on the inside of the dowel can be obtained by drilling the dowel at the appropriate site. The hollow cylinder obtained in this way does not present an internal screw thread. A certain internal structure can be obtained by simple mechanical means, however. The grooves required for spreading are obtained by sawing with a thin saw blade.

EXAMPLE 3

Bone dowels can be produced by means of injection moulding in the following way: A molten mass is produced from polyglycolate granulate and several grams of biocompatible softeners in a specially provided apparatus. After a homogeneous mass is obtained, the liquid molten mass is injected into an injection moulding form at a pressure of approximately 20 bar. This is then cooled. The surface porosity can be set according to the cooling rate. Surface structures with large pores can be obtained by adding gels or volatile reagents (4th order structure), whereas the 2nd and 3rd order structures can be most simply obtained by the shape of the moulding form.

I claim:

1. An implant to support or reinforce bone or to anchor bone screws, artificial implants or implant compounds in a bone, said implant consisting of a body of absorbable, biocompatible material having a hollow cylindrical configuration having a closed end such that said implant is adapted to be fully insertable into the bone and means for spreading out or swelling the implant after being inserted in the bone thus finding a firm support in the surrounding bone.

2. An implant according to claim 1 wherein the main shape of the implant is that of a dowel-like hollow body (10).

3. An implant according to claim 1 wherein the generally cylindrical body has an outer surface having a shape having several stacked, ring-like bulges (16) or semi-spheres along an axis of the body's outer surface.

4. An implant according to claim 3 wherein the generally cylindrical body comprises a plurality of spheres having a diameter between approximately 200 and 3,000 μm.

5. An implant according to claim 3 wherein the diameter of the bulges (16) or the semipheres is between approximately 200 and 3,000 μm.

6. An implant according to claim 1 wherein the implant comprises a tip.

7. An implant according to claim 1 wherein the implant comprises an inner surface which is shaped, the shape being grooves, perforations, threads or elevations.

8. An implant according to claim 1 wherein an outer surface of the generally cylindrical body has a shape having spheres and semi-spheres.

9. An implant according to claim 8 wherein the body comprises a plurality of spheres with a diameter of between 10 and 50 μm.

10. An implant according to claim 8 wherein the outer surface is roughened by a substance selected from the group consisting of embedded tricalcium phosphate and hydroxyl apatite powder.

11. An implant according to claim 1 wherein the implant comprises material selected from the group consisting of inorganic absorbable materials, organic absorbable materials, absorbable plastic and composites of absorbable inorganic and organic materials.

12. An implant according to claim 11 wherein the plastic is a high-strength, biocompatible plastic.

13. An implant according to claim 11 wherein the absorbable organic material is a mixture whose base is selected from the group consisting of polylactates, polyglycolates polypeptides and collagens.

14. An implant according to claim 11 wherein the absorbable inorganic material is selected from the group consisting of apatite, tricalcium phosphate and absorbable ceramic.

15. An implant according to claim 11 wherein the implant consists of a mixture with an absorbable matrix and a filler the filler being selected from the group consisting of an absorbable tricalcium phosphate and a hydroxyl apatite.

16. An implant according to claim 15 wherein the filler consists of spheres approximately 10-200 μin size.

17. An implant according to claim 11 and further comprising reinforcing means, the means being selected from the group consisting of fibers, a fibrous network and a tissue sheath (42), the means being constructed from a material selected from the group consisting of absorbable threads and suture material.

18. An implant according to claim 1 wherein the implant contains an active pharmaceutical agent.

19. An implant according to claim 18 wherein the pharmaceutical agent is selected from the group consisting of an antibiotic and a cytostatic agent and a bone morphogenetic protein and a hemostatic agent and a hormone.

20. An implant according to claim 19 wherein gentamycin is used as the antibiotic.

21. An implant according to claim 1 wherein at least a portion of an outer surface of the implant is coated with a matrix, the matrix consisting of an organic material and a filler, the filler being selected from the group consisting of tricalcium phosphate, bioglass and hydroxyl apatite.

22. An implant according to claim 1 wherein a coating mixture is applied to at least a portion of an outer surface of the body, the mixture comprising an organic matrix, wherein the matrix is selected from the group consisting of collagen, polyglycolate, polylactate and a polypeptide.

23. An implant according to claim 1 wherein the outer side of the implant is coated, the coat containing a pharmaceutical substance.

24. An implant according to claim 23 wherein the pharmaceutical substance is selected from the group consisting of an antibiotic and a cytostatic agent and bone morphogenetic protein and a hemostatic agent.

25. An implant according to claim 24 wherein gentamycin is used as the antibiotic.

26. An implant according to claim 8 wherein the body is coated with a mixture consisting of a plurality of spheres and a matrix coat, wherein the matrix is an organic material selected from the group consisting of collagen, polyglycolate, polylactate and polypeptide.

27. An implant to support or reinforce bone or to anchor bone screws, artificial implants or implant compounds in a bone, said implant consisting of a body of absorbable, biocompatible material, said implant having a generally cylindrical configuration being fully insertable into the bone and comprising a double-walled stocking cage in which spheres 500–5000 μm in size are held thus forming a lumen into which screw means can be screwed in or a cylinder or wedge can be inserted for spreading out the implant after being inserted in the bone.

28. An implant according to claim 1 wherein the implant includes means for screwing it into the bone.

29. An implant according to claim 1 wherein the shape of a portion of a shaped outer surface is selected from the group consisting of grooves, perforations, threads or elevations.

30. An implant according to claim 7 wherein the internal structure is an internal screw thread (20) or a thread-like internal structure.

31. An implant according to claim 8 wherein the shaped surface comprises a plurality of semi-spheres with a diameter of between 10 and 50 μm.

32. An implant according to claim 11 wherein the implant is formed from at least one of the group consisting of a mixture of organic materials and at least one organic material in combination with at least on inorganic absorbable material selected from the group consisting of apatites or absorbable ceramics.

33. An implant according to claim 1 wherein the outer side of the implant is coated, the coat consisting of an organic matrix with inorganic filler components.

34. An implant according to claim 1 wherein the generally cylindrical body comprises a plurality of contiguous spheres, and means for holding the spheres in close proximity to form the body.

35. An implant according to claim 1 wherein the outer surface of the implant has a shape selected from the group consisting of grooves, perforations, threads, thread-like elevations, pores or microroughnesses.

* * * * *

UNITED STATES PATENT AND TRADEMARK OFFICE
CERTIFICATE OF CORRECTION

PATENT NO. : 5,084,050
DATED : January 28, 1992
INVENTOR(S) : Klaus Draenert

It is certified that error appears in the above-identified patent and that said Letters Patent is hereby corrected as shown below:

Col. 10, Line 67, delete "hormone.", insert "hormone as the pharmaceutical agent."

Signed and Sealed this

Twenty-fifth Day of May, 1993

Attest:

MICHAEL K. KIRK

Attesting Officer

Acting Commissioner of Patents and Trademarks